United States Patent
Xiao

(10) Patent No.: US 6,919,094 B1
(45) Date of Patent: Jul. 19, 2005

(54) COMPOSITION OF MEDICINE FOR TREATING HEADACHE DISEASE AND PROCESS OF PREPARATION AND USES THEREOF

(75) Inventor: Wei Xiao, Jiangsu (CN)

(73) Assignee: Jiangsu Kanion Pharmaceutical Co., Ltd., Lianyungang (CN)

( * ) Notice: Subject to any disclaimer, the term of this patent is extended or adjusted under 35 U.S.C. 154(b) by 0 days.

(21) Appl. No.: 10/380,273

(22) PCT Filed: Sep. 12, 2000

(86) PCT No.: PCT/CN00/00272
§ 371 (c)(1),
(2), (4) Date: Jul. 23, 2003

(87) PCT Pub. No.: WO02/22143
PCT Pub. Date: Mar. 21, 2002

(51) Int. Cl.$^7$ ................................. A61K 35/78
(52) U.S. Cl. ........................ 424/725; 424/773
(58) Field of Search ................. 424/725, 773

(56) References Cited

FOREIGN PATENT DOCUMENTS

CN  A1076620  9/1993
CN  A1235047  11/1999

OTHER PUBLICATIONS

Derwent English abstract of Chinese Pat. No. 1181973 A (1998).*
English abstract of Chinese Pat. No. 1117866 A (1996).*
www.herbasin.com/database/chuanxiong.htm; accessed Sep. 29, 2004.*
www.herbasin.com/database/tianma.htm; accessed Sep. 29, 2004.*
www.meridianhealth.com/index.cfm/HealthContent/adult/neuro.vascache.cfm; accessed Sep. 29, 2004.*

* cited by examiner

Primary Examiner—Susan D. Coe
(74) Attorney, Agent, or Firm—Burns, Doane, Swecker & Mathis, L.L.P.

(57) ABSTRACT

This invention relates to a medicine combination used to treat headache, which is made up of Chuanxiong and Tianma in a certain scientific weight proportion. The medicine combination can be made into any commonly used dosage form. The invention also provides other applications of this medicine combination in the production of an anti-oxidative drug, an antihypertensive drug, a platelet antiaggregation drug, an antithrombosis drug and an anticoagulant.

13 Claims, No Drawings

2

COMPOSITION OF MEDICINE FOR TREATING HEADACHE DISEASE AND PROCESS OF PREPARATION AND USES THEREOF

FIELD OF THE INVENTION

This invention is related to a kind of combination of medicines to treat headache, especially a combination of medicines which are made from the Chinese herbal medicine that can cure headache. This invention is also related to the preparation of this medicine combination and applications in the pharmaceutical field—the traditional Chinese medicine field.

BACKGROUND OF THE INVENTION

Headache, especially the vascular headache, is a commonly encountered disease and frequently occurring disease. Vascular headache includes the type of vascular hemicrania and the type of vascular nonhemicrania. Based on the domestic and international statistical data, the incidence rate of vascular headache is about 4–6%, while the incidence rate in China is about 6.3%. Estimated on this data, the number of the patients suffering from the vascular headache in China is about 6,000,000–8,000,000, while the actual number may be even more. This disease seriously affects people's usual work, study, health and life.

In the recent decades, more and more attention was paid to this disease in the modern medicine. The majority of the scholars believe that the mechanism of vascular headache is related to the genetic factors, the dysfunction of the cerebrovascular relaxation-contraction movement, the vitium of the blood brain barrier, the dysfunction of the internal secretion, the concentration change of the bradykinin, 5-HT, histamine and the other vaso-active substances, the enhancement of the platelet aggregative function and adhesive function. By now, the main therapies of the vascular headache include: vasoconstrictor, antiserotonin, inhibitor of the platelet aggregation, antihistamine, β-receptor blocking agent, tranquilizer, several kinds of hormone, oxygen therapy in the high pressure situation and the surgical therapies such as the cutting off the sympathetic nerve and the ligation of the special vessels out of skull. But the effects are not very ideal, especially the effects in the future. Additionally, all these therapies have many side effects.

SUMMARY OF THE INVENTION

By taking advantage of the plentifulness of the Chinese herbal medicine in combination with the modern pharmacological, toxicological and clinical research findings of the Chinese herb medicine, we selected two herbs: Chuanxiongiong (Rhizome of chuanxiong)—with the function of activating blood circulation to dissipate blood stasis, and Tianma (Rhizome of tall gastrodia)—with the function of calming the wind and relieving convulsion and spasm, then searched out a scientific way of compatibility and an elaborate preparation method. On these bases we made out this invention's technical proposal.

The first purpose of this invention is to provide a medicine combination, which has a remarkable function of anticoagulant, antianoxic, depressurizing, calming and antalgic, to treat headache.

The second purpose of this invention is to provide the special preparation of this medicine combination.

The third purpose of this invention is to provide the application of this medicine combination in the manufacture of other medicines used to treat headache. These medicines include the drug to treat the vascular headache and the drug to treat the neural headache.

The fourth purpose of this invention is to provide the application of this medicine combination in the manufacture of the antianoxic drug.

The fifth purpose of this invention is to provide the application of this medicine combination in the manufacture of antihypertensive drug.

The sixth purpose of this invention is to provide the application of this medicine combination in the manufacture of the platelet anticoagulant.

The seventh purpose of this invention is to provide the application of this medicine combination in the manufacture of the anti-thrombosis drug.

The eighth purpose of this invention is to provide the application of this medicine combination in the manufacture of the anticoagulant.

The medicine combination mentioned in this invention was composed by the herbs of the special weight as following:

Chuanxiongiong 10 g–25 g
Tianma 1.5 g–8 g
The better weight proportion of the two herbs is that:
Chuanxiongiong 8 g–15 g
Tianma 2 g–6 g
The best weight proportion of the two herbs is that:
Chuanxiongiong 10 g
Tianma 2.5 g According to the special compatibility of the herbs mentioned above and by the regular pharmaceutics method, the medicine combination in this invention can be made into any of the normal dosage forms, such as the capsule, the water-soluble powder, the tablet, the pellet, the oral liquid and the drop pills. The optimal form is the capsule. In the producing process, a regular excipient such as amylo and silicon dioxide can be added in the medicine combination.

The preparation of the medicine combination of the present invention is that: in the proportion of the present invention, Chuanxiongiong and Tianma of the special weight are dehydrated, smashed and mixed together. The mixed powder is extracted in the cycling 90% alcohol solution. The extracted liquids are merged and filtrated. Then the extracted solution is condensed to the clear cream at the relative density of 1.27 and at the degree ranged from 55° C. to 60° C. The gruffs are cooked in water, and then the extracted water solutions are merged and filtrated. The solution is condensed to the clear cream at the relative density of 1.27 and at the temperature ranging from 55° C. to 60° C. and then all the clear cream is combined together. The excipient is added into the mixed cream, and then the new cream is dehydrated in the vacuum, smashed and filtrated. Capsule the medicine powder and obtain the final medicine capsule.

In the preparation mentioned, the 90% alcohol solution can be used twice to extract the mixed raw herbs powder, and each time for 2 hours. The gruffs can be cooked twice, and each time for 1 hour.

The invention medicine has the function of curing the wind syndrome of head, the dizziness and blurred vision. It is also good at dispelling the wind and cold in the Yang channel, dispersing and expelling the phlegm in the chest, and treating the splitting and normal headache. It can also relieve the body constriction and listlessness, refresh the mind, and open the orifice. It has an obvious effect on the cardiovascular system, the blood system and the central nervous system. The effects on these systems are as follows:

1. The effect on the cardiovascular system: (1) the antianoxic function: The invention medicine can enhance the mouse's tolerance to the anoxic situation in the normal atmosphere pressure, and prolong the time of death in the oxygen free environment. It can lower the heart's time-tension index (TTI) of the anesthetic dog, and reduce the cardiac muscle's oxygen consumption. (2) The function of lowering BP: Not only can it lower the BP of the normal rat and dog in the anesthetic condition, but also lowers the BP, renin activity and the aldosterone concentration of the renal hypertension rat (Goldblatt rat) and the spontaneous hypertension rat. The fact indicates that the effect of lowering the BP is accomplished by regulating the RAS system.

2. The effect on the blood system: (1) The function of inhibiting the platelet aggregation: This invention medicine can not only suppress the rabbit's and rat's platelet aggregation induced by the ADP, but suppress the rat's experimental thrombosis. (2) The function of anticoagulation: the medicine can prolong the rat's thrombin time (TT) and the kaolin partial thrombin time (KPTT), and enhance the anticoagulation activity of the plasma.

3. The effect on the central nervous system: (1) The function of tranquilizing; (2) The function of antalgic: it can relieve the pain caused by the heat, the electricity and the chemical reagent.

Another advantage of this invention medicine lies in that that Chuanxiong has the function of activating blood circulation to dissipate blood stasis and meliorating the blood circulation of the brain, and that Tianma has the function of relieving the pain caused by contracture and spasm and meliorating the vascular function. When the two herbs are used together, they can create a synergetic effect. Chuanxiong, which can activate blood circulation and dissipate blood stasis, makes the blood flow smoothly in the vessel. Additionally, it can promote circulation of Qi to relieve the pain. It is the king medicine in the invention medicine combination. Tianma, which has the even nature and the sweet flavor, can calm the wind and arrest convulsion. It is good at curing the dizziness, the wind syndrome of head, the headache and the numbness of the limbs. It is good at going to the upper orifices and makes up the best compatibility with Chuanxiong to treat vascular headache. The combination of the two herbs has a good effect to relieve the tendencies of "dense, congregate, stasis", that is the characteristic of the blood-stasis-type patients. The compound has a better effect than the single herb. Toxicology experiments indicated that: the Daxiong (made by the method of the present invention and named after Daxiong capsule) capsule's $LD_{50}$ amounts by single administration on mouse are as follows: intravenous injection (4.01±0.41 g/kg); intraabdominal injection (14.03±1.12 g/kg); stomach douche (52.19±6.36 g/kg). The Daxiong capsule's LD50 amount by single administration on rat by oral administration is 57.36±4.82 g/kg. Rats which have taken the Daxiong capsule continuously on the amount of 7.5, 15.0 g/kg for 3 months showed no toxic reaction. This amount is 10–20 times of the clinical dosage.

In addition, the clinical experiment proved that: the Daxiong capsule's total effective rate is 89.05%, which is remarkable higher than 72% effective rate of the commonly used similar medicine—"Yuntongding". The total effective rate in patients with hyperactivity of liver-yang is 90.91%, while the rate in the patients of internal accumulation of blood stasis is 72%. The effective rate is obviously higher than that of the "yuntongding".

DETAILED DESCRIPTION OF THE PREFERRED EMBODIMENTS

Practice Example 1

Chuanxiongiong 784 g and Tianma 196 g were taken, then the raw herbs were dehydrated, smashed and mixed. The powder was extracted with the 90% alcohol solute twice, each time for 2 hours. The extracted solution was collected, then filtered and the colature condensed to the clear cream at the relative density of 1.27 (55–60° C.) The gruffs were cooked in the water twice, each time for 1 hour. The extracting solution was collected and filtered then the solution was condensed to the clear cream at the relative density of 1.27(55–60° C.). The clear cream was mixed together with the cream mentioned above, then silicon dioxide 49 g was added to it. The medicine was dehydrated in the vacuum, smashed and the powder filtrated, then medicine was capsulated into 1000 capsules.

Practice Example 2

The Invention Medicine's Effect on the Cardiovascular System

1. The influence on mice in the situation of anoxic and normal atmosphere pressure: male NIH mice weighing 18–22 g were divided into 7 groups at random, and 10 mice to a group. After feeding the mice the Daxiong capsule for 0.5 h, 1.2 h, 3 h and 4 h, the mice were enclosed in conical flasks—each conical flask's volume is 165 ml and each flask has 2 g soda lime, which can absorb the $CO_2$ and the vapor. The results are shown in Table 1. According to the data, the Daxiong capsule can enhance the mice's endurance to the anoxic situation. Compared with the control group, the mice fed with the Daxiong capsule on the dosage of 7.5 g/kg, 15.0 g/kg survived 8.87% (P>0.05), 20.44% (p<0.010) longer than the mice in the control group. This effect lasted 3 hours.

TABLE 1

Daxiong capsule's influence to the mice's survival time in the situation of anoxic at normal atmosphere pressure.

| Medicine | Dosage (g/kg) | Administration way | Administration time | Number of mouse | Survival time |
|---|---|---|---|---|---|
| Control group | — | PO | 0.5 | 10 | 20'18" ± 1'5" |
| Daxiong capsule | 7.5 | PO | 0.5 | 10 | 22'6" ± 1'7" |
| Daxiong capsule | 15.0 | PO | 0.5 | 10 | 24'27" ± 46"** |
| Daxiong capsule | 15.0 | PO | 1 | 10 | 24'34" ± 1'36"* |
| Daxiong capsule | 15.0 | PO | 2 | 10 | 24'39" ± 1'37"* |
| Daxiong capsule | 15.0 | PO | 3 | 10 | 24'31" ± 1'10"* |
| Daxiong capsule | 15.0 | PO | 4 | 10 | 19'47" ± 1'2" |

Note 1):
Compared to the control group, * means P < 0.05,  means P < 0.01, * means P < 0.001, and these symbols will represent the same meaning in the other practice examples following.

2. The blood-pressure-lowering function 2.1 The acute blood-pressure-lowering function on anaesthetic dogs: Mongrels weighing 13–18 kg, including males and females, were chosen, then the mongrels were anesthetized by injecting the pentobarbital sodium into the vein on the dosage of 30 mg/kg. The pressure transducer was connected to the mongrels' common carotid artery, then the SBP and MBP were recorded by the PPF-5 carrier amplifier, at the same time recording the II lead of the ECG by the RB-5 biophysical amplifier and the HR by the RT-5 cardiotachometer. By calculating the square root of SBP and HR's product, the TTI (time tension index) was deduced. Memorizing the indexes in the RM-86 recorder, five minutes after the indexes turning to be stable, the Daxiong capsule solution (all the solution was the invention medicine dissolved in 20 ml 0.9% NS) was injected in the mongrels' femoral vein on the dosage of 62.5 mg/kg, 125.0 mg/kg, 250.0 mg/kg. After the injection, HR was obviously reduced, and the peak values of the decreasing amplitude are 4.8% (p<0.01), 34.1% (P<0.05), 48.9% (p<0.001), 32.3% (P<0.01). The influence of Daxiong capsule on the HR, MBP, TTI can remain about 0.5 h. Additionally, the process has a certain dose-effect relationship and a time-effect relationship. Daxiong capsule has no effect on the ECG. The results are shown in Table 2.

rats were anestetized by injecting sodium pentobarbital into the abdominal cavity on the dosage of 30 mg/kg. The left renal artery was clamped to be narrow by the silver clip with the inside diameter of 0.20 mm or 0.25 mm, and the right kidney left untouched. Five weeks later, the rats were divided into groups equally on the level of BP and BW. The treatment groups were injected with Daxiong capsule solution into the stomach once a day for 3 weeks on the dosage of 5 g/kg, 10 g/kg, 20 g/kg, while the control group was injected with distilled water on the same dosage. Record the BP and HR once a week by the CRS-III BP-HR-meter to observe the change process of HB. The BP of the rats which were fed with Daxiong capsule on the dosage of 20 g/kg for 1 week lowered for 16.25% (P<0.01), compared with the control group, while it took 3 weeks for the group fed on the dosage of 10 g/kg to lower BP to the same level. The group

TABLE 2

The Daxiong capsule's influence on the HR, MBR, TTI of the anesthetic dogs

| Index | medicine | dosage (mg/kg) | number of dog | before administration | after administration | | | | |
|---|---|---|---|---|---|---|---|---|---|
| | | | | | 1' | 5' | 10' | 15' | 30' |
| HR (times/min) | Control group | — | 6 | 183.4 ± 4.2 | 183.4 ± 4.2 | 184.6 ± 3.8 | 184.2 ± 3.8 | 184.2 ± 3.8 | 183.0 ± 3.9 |
| | Daxiong capsule | 62.5 | 6 | 179.8 ± 10.5 | 177.6 ± 11.7 | 170.3 ± 10.5* | 165.0 ± 10.6*** | 169.7 ± 13.3* | 179.5 ± 17.8 |
| | Daxiong capsule | 125.0 | 6 | 168.3 ± 7.3 | 153.2 ± 9.9* | 149.7 ± 10.3* | 151.5 ± 7.1*** | 151.7 ± 8.2*** | 157.8 ± 9.4* |
| | Daxiong capsule | 250.0 | 6 | 163.7 ± 13.2 | 132.5 ± 15.6** | 135.2 ± 13.9* | 138.0 ± 13.9* | 141.8 ± 13.3* | 152.8 ± 13.4* |
| MBP (mmHg) | control group | — | 6 | 146.8 ± 4.9 | 148.8 ± 4.6 | 148.8 ± 5.8 | 150.0 ± 5.2 | 149.6 ± 5.2 | 148.8 ± 4.6 |
| | Daxiong capsule | 62.5 | 6 | 140.7 ± 6.7 | 134.0 ± 7.8** | 135.0 ± 7.0** | 134.0 ± 7.9*** | 134.3 ± 7.2** | 135.0 ± 6.2 |
| | Daxiong capsule | 125.0 | 6 | 147.3 ± 3.4 | 97.0 ± 15.8* | 115.7 ± 8.4* | 123.7 ± 6.3* | 127.7 ± 6.2* | 136.7 ± 4.7* |
| | Daxiong capsule | 250.0 | 6 | 149.3 ± 7.1 | 76.3 ± 13.5*** | 106.7 ± 13.1* | 117.0 ± 12.1* | 124.0 ± 10.6* | 138.3 ± 7.8* |
| TTI | control group | — | 6 | 174.3 ± 4.5 | 176.6 ± 4.0 | 177.7 ± 4.4 | 178.1 ± 3.4 | 177.9 ± 4.6 | 175.6 ± 4.3 |
| | Daxiong capsule | 62.5 | 6 | 166.6 ± 8.0 | 163.1 ± 8.8 | 159.6 ± 8.5* | 160.3 ± 7.9*** | 157.8 ± 9.0* | 165.1 ± 11.5 |
| | Daxiong capsule | 125.0 | 6 | 167.6 ± 5.1 | 136.4 ± 16.6 | 145.9 ± 12.1 | 150.3 ± 8.7* | 151.3 ± 9.0* | 158.3 ± 7.3* |
| | Daxiong capsule | 250.0 | 6 | 164.7 ± 8.1 | 111.5 ± 12.6** | 128.4 ± 12.4** | 137.0 ± 11.4** | 142.2 ± 10.7* | 154.8 ± 9.2** |

2.2 The blood-pressure-lowering function on the Goldblatt rat. Wistar rats weighing 160–200 g were chosen and the fed with the positive compare medicine also had an obvious BP decrease. The results are shown in Table 3.

TABLE 3

Daxiong capsule's influence on the BP (mmHg) of the renal hypertension rats

| medicine | dose (g/kg) | administration way | number of rats | before administration | after administration | | | |
|---|---|---|---|---|---|---|---|---|
| | | | | | 1/2 (week) | 1 (week) | 2 (week) | 3 (week) |
| (control group) distilled water | (same volume) | PO | 6 | 189.0 ± 4.8 | 214.5 ± 9.7 | 220.9 ± 19.2 | 229.9 ± 7.0 | 245.4 ± 7.9 |
| Daxiong capsule | 5 | PO | 8 | 191.2 ± 4.0 | 212.4 ± 9.5 | 220.8 ± 15.3 | 215.5 ± 10.2 | 235.2 ± 9.3 |
| Daxiong capsule | 10 | PO | 8 | 190.0 ± 4.4 | 203.3 ± 7.4 | 195.3 ± 8.7 | 204.5 ± 13.5 | 205.5 ± 7.6** |
| Daxiong capsule | 20 | PO | 8 | 190.5 ± 4.3 | 188.1 ± 10.9 | 191.7 ± 10.7** | 190.1 ± 11.6*** | 195.2 ± 15.3* |
| Captopril | 2 × 10-2 | PO | 6 | 190.8 ± 4.9 | 155.6 ± 5.2** | 147.8 ± 7.1** | 151.1 ± 12.9** | 143.5 ± 11.5** |

2.3 The influence to the BP, PRA, AID of the spontaneous hypertension rat (SHR): 3-month-old SHR weighing about 150 g were divided into groups according to the BP, BW. The administration way, dosage, time and the measure method were the same as the experiment above. At the same time, 3-month-age normal WKY rats were chosen as the control group. 2 hours after the final administration, the rats were decapitated and the blood collected. The activity of renin and aldosterone were measured by the way of ELISA. The results demonstrated that the BP of the rats fed with the Daxiong capsule on the dosage of 5 g/kg, 10 g/kg, 20 g/kg for one week had a remarkable decrease by 3.35% ($p<0.05$), 8.02% ($p<0.01$), 11.19% ($p<0.001$). The decrease amplitude is on a direct ratio to the dosage and remained at a steady level for three weeks. (Table 4). Additionally, the PRA and AID were on the obviously lower level than the control group. (Table 5)

percents between the treatment group and the control group at the $5^{th}$ minute. The results are shown in Table 6. Daxiong capsule can remarkably inhibit the rabbit platelet's aggregation character: at the drug concentration 1.95 mg/ml, 3.90 mg/ml, the platelet aggregation percents were 46.73±1.95% ($P<0.01$), 37.98±3.00% ($P<0.001$)

TABLE 6

Daxiong capsule's influence on the rabbit platelet aggregation character.

| medicine | Concentration (mg/ml) | number of experiments | aggregation percent (%) |
|---|---|---|---|
| Control group | | 9 | 57.73 ± 2.39 |
| Daxiong capsule | 1.95 | 6 | 46.73 ± 1.59** |
| Daxiong capsule | 3.90 | 6 | 37.98 ± 8.00*** |
| Aspirin | 0.27 | 6 | 39.94 ± 2.05*** |

TABLE 4

Daxiong capsule's influence to the HB of the SHR

| medicine | dosage (g/kg) | administration way | number of mice | before administration | 1/2 (week) | 1 (week) | 2 (week) | 3 (week) |
|---|---|---|---|---|---|---|---|---|
| normal group | same volume distilled water | PO | 13 | 112.8 ± 1.5 | 111.2 ± 1.0 | 115.1 ± 1.3 | 111.5 ± 5.3 | 110.7 ± 1.3 |
| control group | same volume distilled water | PO | 13 | 170.5 ± 2.5 | 171.5 ± 2.4 | 173.3 ± 1.4 | 178.5 ± 1.8 | 180.1 ± 2.1 |
| Daxiong capsule | 5 | PO | 13 | 170.8 ± 2.4 | 168.4 ± 2.3 | 167.5 ± 2.3 | 170.4 ± 3.0 | 165.2 ± 3.2 |
| Daxiong capsule | 10 | PO | 13 | 170.6 ± 2.9 | 160.9 ± 2.5** | 159.4 ± 1.6** | 159.2 ± 2.3 | 157.3 ± 1.9*** |
| Daxiong capsule | 20 | PO | 13 | 170.1 ± 2.9 | 159.2 ± 2.7** | 153.9 ± 2.8*** | 154.3 ± 1.4** | 151.8 ± 1.4*** |
| captopril | 2 × 10-2 | PO | 12 | 170.5 ± 2.9 | 113.5 ± 3.9*** | 138.2 ± 3.6*** | 142.3 ± 1.8*** | 140.0 ± 2.0*** |

TABLE 5

Daxiong capsule's influence to the PAR, AID of the SHR

| medicine | dosage (g/kg) | administration way | number of mice | PRA (ng/ml/h) | AID (ng/ml) |
|---|---|---|---|---|---|
| normal group | — | — | 13 | 4.66 ± 0.69 | — |
| control group | — | PO | 13 | 9.81 ± 0.98 | 2.78 ± 0.10 |
| Daxiong capsule | 1.25 | PO | 13 | 4.78 ± 0.77*** | 1.94 ± 0.16*** |
| Daxiong capsule | 2.50 | PO | 13 | 2.69 ± 0.67*** | 2.29 ± 0.12** |

Practice Example 3

This Medicine's Influence to the Blood System

1 The influence on the platelet's aggregative character.

1.1 The influence on the rabbit platelet's aggregative character: Rabbit platelet plasma was prepared according to the Csalay's method. Lucid rabbit's blood was collected by carotid arterial cannula, then the blood was mingled with 3.8% sodium citrate in proportion of 9:1 to anticoagulate. The mixture was centrifuged on the speed of 1000 rpm for 5 minutes then at the speed of 3000 rpm for 10 minutes. The blood plasma was separated into the platelet-rich plasma and the platelet-absent plasma. When conducting the measurement, the platelet aggregation percent was regulated to 50–60%. The platelet aggregation experiment was performed according to the Born's method by the PPP autobalance platelet-aggregation-machine (type SPA-3), keeping the concentrate of ADP(the aggregation inducer) at 12 $\mu$M, then collecting the data and comparing the aggregation 1.2 The influence on the rat platelet aggregation character: Wistar rats weighing 180–210 g, including males and females, were chosen then fed with Daxiong capsule by gastric administration. 1.5 hour after the administration, the blood from the abdominal aorta was collected on the condition of anesthesia by ether. The platelet plasma was prepared by the same method mentioned above, and the PLT aggregation experiment performed by the same machine with a different ADP concentrate of 2.8 $\mu$M. Comparing the two aggregation percents, we got the results shown in Table 7. As the table shows, eating Daxiong capsule can inhibit the rat PLT aggregation. At the dosage of 5 g/kg, 10 g/kg, the rat's largest platelet aggregation percents were 37.35±5.06% ($P<0.01$), 631.14±5.02% ($P<0.01$).

TABLE 7

Daxiong capsule's influence on the rat platelet aggregation character.

| medicine | dosage (g/kg) | administration way | number of rat | platelet aggregation percent (max) |
|---|---|---|---|---|
| Control group | | PO | 6 | 54.00 ± 4.23 |
| Daxiong capsule | 5 | PO | 6 | 37.35 ± 5.06* |
| Daxiong capsule | 10 | PO | 6 | 31.14 ± 5.02** |
| Aspirin | 2.7 × 10-2 | PO | 6 | 31.06 ± 3.80** |

1.3 The influence on the rat's experimental thrombosis: Male Wistar rats weighing 270–370 g were chosen to be anaesthetized by belly injection of sodium pentobarbital on the dosage of 50 mg/kg, then the rats were fixed at the supine position and the right common carotid artery and the left external jugular vein were detached. A polyvinyl pipe of 19.5 cm long with the inside diameter of 1.5 mm embedded in a 5.0 cm-long type 4 suture and filled with the solution of heparin and normal saline (25 μ/kg) was inserted into the right common carotid artery one end and the left external jugular vein the other end. The pipes were opened, then the extracorporeal circulations were built up 1 hour after the rats were fed with Daxiong capsule. 15 minutes later, the pipe was closed, the suture taken out and the greenweight measured. The results are shown in Table 8. Daxiong capsule has a remarkable inhibitory action on the thrombosis. The inhibitory ratios were 15.39% (P<0.25), 24.33% (P<0.01) on the dosage of 5 g/kg, 10 g/kg.

TABLE 8

Daxiong capsule's influence on the rat experimental thrombosis

| medicine | dosage (g/kg) | administration way | number of rat | greenweight of thrombus (mg) |
|---|---|---|---|---|
| Control group | — | PO | 10 | 25.40 ± 1.10 |
| Daxiong capsule | 5 | PO | 10 | 21.49 ± 1.08* |
| Daxiong capsule | 10 | PO | 10 | 19.22 ± 1.62** |
| Aspirin | 0.05 | iv | 6 | 18.28 ± 1.28* |

2. The influence on the TT and KPTT of the rat. Wistar rats weighing 250–300 g were chosen and blood sampled from abdominal aorta under the anesthetic condition by ether. The blood was mixed with the 3.8% sodium citrate in proportion of 9:1 and centrifuged (3000 rpm×20 min) to get the no-platelet plasma. The experiments following were done on the PPP autobalance platelet-aggregation machine (type SPA-3):

(1) TT measurement: 0.2 ml of thrombase solution (the control group's TT was regulated to 6–18 s with the same thrombase solution) was added to the medicine in the cuvette to be incubated together. 5 minutes later 0.1 ml of plasma was added in the cuvette, then the time quantum from this point to the time that the solution's optical density suddenly changed was recorded as the TT.

(2) KPTT measurement: 0.1 ml of kaolin partial thrombase suspending liquid (the KPTT of the control group was regulated to 36–38 s with the same suspending liquid) and 0.1 ml plasma were added into the cuvette, which contained with the medicine. The mixture was incubated for 3 min. 0.1 ml of 0.03 M $NaCl_2$ was added in the mixture and the time quantum from this point to the time that the suspending liquid's optical density suddenly changed was recorded as the KPTT. The experiment results are shown in Table 9.

The TT of the treatment groups prolonged by 18.79% (P<0.01), 30.30% (P<0.001) on the dosages of 1.25 mg/ml, 2.50 mg/ml than the TT of the control group, while the APTT prolonged by 5.35% (P>0.05), 10.16% (p<0.05) compared to the control group. The result indicated that Daxiong capsule can remarkably prolong the blood clotting time and enhance the activity of the blood anticoagulation.

TABLE 9

Daxiong capsule's influence on the rat TT and KPTT.

| medicine | drug concentration (mg/ml) | number of experiment | TT (s) | KPTT (s) |
|---|---|---|---|---|
| control group | — | 7 | 16.5 ± 0.5 | 37.4 ± 0.6 |
| Daxiong capsule | 1.25 | 7 | 19.6 ± 0.6** | 39.4 ± 2.4 |
| Daxiong capsule | 2.50 | 7 | 21.5 ± 0.6*** | 41.2 ± 1.2* |

Practice Example 4

The Invention Medicine's Influence on the Central Nervous System 1.1 The influence on the mouse's spontaneous activity. Kunming mice weighing 18–22 g were chosen and divided into groups at random. Each group was made up of 10 mice. The mice were put into the three-optical-track mouse activity recorder (type GJ-7902) to count the amount of mice's spontaneous activity, 50 minutes after the treatment groups' mice were fed with the medicine on the dosage of 2.5 g/kg, 5.0 g/kg, 10.0 g/kg and the control group's mice were fed with the same volume distilled water. The results showed that Daxiong capsule can remarkably decrease the normal mice's spontaneous activity. According to the different dosages, the inhibition ratios were 31.41% (P<0.05), 36.54% (P<0.05), 43.90% (P<0.01).

TABLE 10

Daxiong capsule's influence on the mice's spontaneous activity.

| Medicine | Dosage (g/kg) | Administration way | Number of mouse | Amount of spontaneous activity |
|---|---|---|---|---|
| Control group | — | PO | 20 | 378.8 ± 36.9 |
| Daxiong capsule | 2.5 | PO | 10 | 259.8 ± 16.6* |
| Daxiong capsule | 5.0 | PO | 10 | 240.4 ± 31.9* |
| Daxiong capsule | 10.0 | PO | 10 | 212.5 ± 27.5** |
| tetrahydropalmatine | 5 × 10-2 | PO | 10 | 24.3 ± 4.3*** |

1.2 The influence on the mouse's sleep time caused by sodium pentobarbital: Male NIH mice weighing 18–22 g were chosen to be divided into 3 groups, 10 mice each group. The mice in treatment group were injected with a solution of Daxiong capsule into the abdominal cavity on the dosage of 1.25 g/kg, 2.5 g/kg, while the mice in the control group were injected the same volume of normal saline. Ten minutes later, each mouse was injected with sodium pentobarbital on the dosage of 35 mg/kg. The time when the righting reflex disappeared was recorded. The results proved that Daxiong capsule can synergize the effect of the sodium pentobarbital and prolong the sleep time caused by the sodium pentobarbital (Table 11). According to the different dosage, the sleep times were prolonged 48.04% (P<0.05), 119.62% (P<0.001), compared to the control group.

TABLE 11

Daxiong capsule's influence on the mice's sleep time.

| Medicine | Dosage (g/kg) | Administration way | Number of mouse | Sleep time |
|---|---|---|---|---|
| Control group | — | ip | 10 | 15'43" ± 3'44" |
| Daxiong capsule | 1.25 | ip | 10 | 23'16" ± 3'6"* |
| Daxiong capsule | 2.50 | ip | 10 | 34'31" ± 2'31"*** |

2 The Function of Antalgic 2.1 The influence on the mouse's reaction to the heat: The experiment referred to the mouse hot-plate method: female NIH mice weighing 18–22 g were put on the type CS501 ultra thermostat's metallic plate, on which the temperature was 55.0±0.5° C. The action of sucking the postpedes and jumping were concerned as the indexes to the pain caused by the heat and the shortest time when the mouse shown the indexes was defined as the pain threshold. The sensitive mice whose pain threshold were shorter than 30 s were chosen and divided into 4 groups according to their pain threshold, each group including 10 mice. The mice were injected with the solution of Daxiong capsule into the abdominal cavity on the dosage of 2.5 g/kg, 5.0 g/kg, then the pain thresholds were measured at time of 0.5 h, 1 h, 3 h and 5 h after the administration. If the threshold was beyond 60 s, it would be recorded as 60 s. The results are shown in Table 12. Daxiong capsule can improve the mouse's pain threshold remarkably, and the effect-dose relationship, time-dose relationship were both the direct ratio. The group in which the mice were fed with Daxiong capsule on the dosage of 2.5 g/kg improved the pain threshold by 87.68% ($p<0.01$), and the effect lasted 1 hour. The group on the dosage of 5.0 g/kg improved the pain threshold by 148.74% ($p<0.001$), and the effect lasted 5 hours.

electricity was switched on and the time when the mouse shrieks was chosen as the index of pain threshold. The sensitive mice whose pain thresholds were shorter than 15 s were chosen to do the experiment. The mice were fed with Daxiong capsule on the dosages of 5 g/kg, 10 g/kg, then the pain thresholds were recorded 60 minutes after the administration. If the pain threshold was longer than 45 s, the pain threshold would be recorded as 45 s. The results proved that Daxiong capsule could improve the mice's pain thresholds remarkably in the electrostimulation experiment. On the dosages of 5 g/kg, 10 g/kg, the pain thresholds were improved by 68.42% ($p<0.05$), 166.67% ($p<0.01$).

TABLE 12

Daxiong capsule's influence on the mouse's pain threshold (hot-plate method)

| Medicine | dosage (g/kg) | administration way | number of mouse | before administration | after administration | | | |
|---|---|---|---|---|---|---|---|---|
| | | | | | 1/2 (h) | 1 (h) | 3 (h) | 5 (h) |
| Control group | — | ip | 10 | 20.3 ± 1.2 | 23.1 ± 2.3 | 20.0 ± 2.3 | 20.0 ± 2.2 | 18.5 ± 1.8 |
| Daxiong capsule | 2.5 | ip | 10 | 20.3 ± 1.2 | 1.8 ± 2.5* | 38.0 ± 3.2** | 30.6 ± 4.9 | 29.3 ± 4.8 |
| Daxiong capsule | 5.0 | ip | 10 | 19.9 ± 0.0 | 38.7 ± 6.8* | 42.7 ± 3.8*** | 44.1 ± 4.6*** | 49.5 ± 3.8*** |
| Morphine hydrochloride | 1.5 × 10-2 | ip | 10 | 22.5 ± 2.4 | >60 | >60 | >60 | >60 |

2.2 The influence on the rat's reaction to the heat. The experiment referred to the rat's tail-whipping method: SD white rats weighing 180–220 g were chosen and the distal ⅓ of their tails were dipped into hot water in which the temperature was regulated to 55.0±0.5° C. by the CS501 ultra thermostat. The tail's whipping out of the water was defined to be the index of pain. The rats were divided equally into 5 groups according to the pain threshold and each group had 9 rats. The rats in the 3 groups (exclude the control group and the positive medicine group) were fed with the Daxiong capsule on the dosage of g/kg, 10 g/kg, 20 g/kg, then the pain thresholds at 0.5 h, 1 h, 2 h and 4 h were measured. The results proved that Daxiong capsule can improve the rat's pain threshold obviously, the effect's intensity and time had a direct relationship with the dosage (Table 13). On the dosage of 0 g/kg, 20 g/kg, Daxiong capsule could improve the pain threshold by 40.63%. ($p<0.05$), 64.52% ($P<0.05$), the duration of effect was 1 h, 4 h.

TABLE 14

Daxiong capsule's influence on the mouse's pain threshold in the electrostimulation experiment

| Medicine | dosage (g/kg) | administration way | number of mouse | before administration | after administration |
|---|---|---|---|---|---|
| Control group | — | PO | 14 | 3.2 ± 0.3 | 3.5 ± 0.7 |
| Daxiong capsule | 5 | PO | 14 | 3.8 ± 0.5 | 6.4 ± 0.4* |
| Daxiong capsule | 10 | PO | 14 | 3.6 ± 0.5 | 9.6 ± 2.3** |
| amino-pyrine | 0.05 | ip | 14 | 4.8 ± 1.0 | 21.3 ± 5.5* |

TABLE 13

Daxiong capsule's influence on the rat's pain threshold (tail-whipping method)

| medicine | dosage (g/kg) | administration way | number of rat | before administration | after administration | | | |
|---|---|---|---|---|---|---|---|---|
| | | | | | 1/2 (h) | 1 (h) | 2 (h) | 4 (h) |
| Control group | — | PO | 9 | 3.1 ± 0.3 | 0.2 ± 0.5 | 3.6 ± 0.3 | 2.6 ± 0.2 | 2.5 ± 0.3 |
| Daxiong Capsule | 2.5 | PO | 9 | 3.2 ± 0.5 | 3.8 ± 0.5 | 3.4 ± 0.3 | 3.2 ± 0.3 | 2.7 ± 0.2 |
| Daxiong Capsule | 5.0 | PO | 9 | 3.2 ± 0.3 | 4.1 ± 0.4 | 4.5 ± 0.4* | 3.2 ± 0.3 | 2.6 ± 0.1 |
| Daxiong capsule | 20 | PO | 9 | 3.1 ± 0.4 | 4.2 ± 0.3* | 5.1 ± 0.6* | 4.7 ± 0.6* | 4.9 ± 0.4* |
| Morphine hydrochloride | 1.5 × 10-2 | PO | 9 | 3.2 ± 0.3 | 9.2 ± 0.8*** | 5.7 ± 0.4** | 4.5 ± 0.4* | 3.3 ± 0.4 |

2.3 The influence on the electrostimulation of mouse: The experiment method adopted was to simulate the mouse's vola with the electricity. Female NIH mice weighing 18–22 g were chosen and put on the conductive copper-wire plate of the YSD-4 multipurpose apparatus's zoopery box. The 2.4 The influence on the chemical stimulation of the mouse: The experiment method was the mouse's body-twisting method. Female NIH mice weighing 18–22 g were divided into groups at random and each group had 10 mice. The mice were fed with the solution of Daxiong capsule on the dosages of 1.25 g/kg, 2.50 g/kg, 5.00 g/kg. 60 minutes later all the mice were injected 0.8% ethanoic acid into the abdominal cavity on the dosage of 0.1 ml/10 g. The number of the mice's body twisting in the following 20 minutes were recorded as the index. The results indicated that Daxiong capsule could reduce this index obviously. The inhibition percents were 27.37% (p<0.01), 54.32% (p<0.001), 76.75% (p<0.001) on the dosages of 1.25 g/kg, 2.50 g/kg, 5.00 g/kg.

TABLE 15

Daxiong capsule's influence on the mouse's body-twisting reaction.

| Medicine | dosage (g/kg) | administration way | number of mouse | twist times |
|---|---|---|---|---|
| Control group | — | PO | 10 | 48.6 ± 2.19 |
| Daxiong capsule | 1.25 | PO | 10 | 35.3 ± 2.94** |
| Daxiong capsule | 2.50 | PO | 10 | 22.2 ± 1.93*** |
| Daxiong capsule | 5.00 | PO | 10 | 11.3 ± 1.94*** |
| aminopyrine | 0.10 | ip | 10 | 2.8 ± 1.3*** |

Practice Example 5

The clinical Test of the Medicine of the Invention

1 General Data 1.1 Case source: All cases were patients treated from January 1993 to July 1993, including 281 in hospital and 157 outpatient, for a total of 438 patients. Among them, Longhua hospital of Shanghai university of T.C.M provided 105 patients, Shuguang hospital of Shanghai university of T.C.M. provided 44 patients, Yueyan hospital of Shanghai university of T.C.M. provided 60 patients, Ruijin hospital of Shanghai No.2 medical university provided 89 patients, the attached hospital of Tianjin medical academy provided 40 patients, the No.2 attached hospital of Tianjin T.C.M. academy provided 40 patients, the No.1 attached hospital of Tianjin T.C.M. academy provided 60 patients (Refer to Table 16). All cases were selected according to choice criterion.

TABLE 16

Case and grouping

| | therapy group | control group | opening group | total |
|---|---|---|---|---|
| Shanghai Yueyang hospital | | | 60 | 60 |
| Shanghai Shuguang hospital | | | 44 | 44 |
| Shanghai Longhua hospital | 36 | 35 | 34 | 105 |
| Shanghai Ruijin hospital | 35 | 35 | 19 | 89 |
| The attached hospital of Tianjin medical academy | | | 40 | 40 |
| The No. 2 attached hospital of Tianjin T.C.M | | | 40 | 40 |
| The No. 1 attached hospital of Tianjin T.C.M | 30 | 30 | | 60 |
| Total | 101 | 100 | 237 | 438 |

1.2 Case Selection 1.2.1 According to diagnose criterion of traditional Chinese medicine as follows:

1.2.1.1 The Diagnose Criterion of Excessive Rise of Liver-yang Syndrome

Main syndrome: (1) headache and dizzy (2) tongue proper is red and tongue fur is light yellow (3) stringy and slippery pulse Secondary syndrome: (1) vexation and irritability (2) insomnia (3) hypochondriac pain and bitter taste in the mouth (4) gloomy mood Diagnosis: the patients possess main syndrome and two of the secondary syndrome (or more than two) can be diagnosed as excessive rise of liver-yang syndrome.

1.2.1.2 The Diagnosis Criterion of Internal Stagnation of the Blood Syndrome

Main syndrome: (1) chronical headache (2) tongue proper is dark purple or have petechia (3) Xi and Se pulse Secondary syndrome: (1) headache like prick (2) the locate of headache is changeless (3) feel sick and vomiting Diagnosis: The patients possess main syndrome and two of the secondary syndrome (or more than two) can be diagnosed as internal stagnation of the blood syndrome.

1.2.2 According to diagnose criterion of western medicine as follows:

Paroxysmal headache, most was pulsation, with the symptom of autonomic nerve dysfunction such as sickness and vomiting, headache paroxysm have intermittence, there can be sight premonitory before headache paroxysm, most with positive family history.

3. Therapy Method 3.1 Drugs

The Daxiong capsule and Yuntongding tablet provided by Tianjin medicine academe (Made by No.2 pharmaceutical factory of Zhoukou district of Henan, approve No.: (86) the medicine approved by ministry of health with the number Z-11)

3.2 Method

There are altogether 438 cases in the group, among them, we chose 201 cases as random double-blinded experiment, other 237 cases as non-random therapy. The random double-blinded group used Daxiong capsule and Yuntongding tablet, non-random group used Daxiong capsule. The dosage is all 4# Tid, the course of treatment is two months.

3.3 Observation standard:

The times and degree of headache paroxysm; the changes of traditional Chinese medicine syndrome; the laboratory examination before and after therapy; rheoencephalogram (REG), Doppler colorful ultrasound (TCD), plasma 5-serotonin (5-HT), plasma thromboxane ($TXB_2$), plasma prostacyclin (PGFla), blood rheology, platelets aggregation. Blood Rt, urine Rt, the examination of liver and kidney function; untoward reaction, toxin and side effect of the medicine.

4. Therapy Result

According to the Guide Principle of Clinical Research with New Medicine (Chinese Medicine)

4.1 General curative effect: The 438 cases of this group randomly grouping, double-blinded compare the therapy result, the group using Daxiong capsule is 101 cases, apparent 32 cases, efficacy 57 cases, inefficacy 12 cases, effective rate is 88.11%; control group 100 cases, apparent 11 cases, efficacy 61 cases, inefficacy 25 cases, effective rate is 72%; opening group 237 cases, apparent 70 cases, efficacy 142 cases, inefficacy 25 cases, effective rate is 89.45%. The average effective rate of Daxiong capsule is 89.05%, apparent rate is 0.18%. Details are shown in Table 17

TABLE 17

Curative effect analysis

| | total | apparent | | efficacy | | inefficacy | | General effective rate |
|---|---|---|---|---|---|---|---|---|
| | | number | % | number | % | number | % | |
| Treat group | 101 | 32 | 31.68 | 57 | 56.43 | 12 | 11.88 | 88.11 |
| control group | 100 | 11 | 11.00 | 61 | 61.00 | 28 | 28.00 | 72.00 |
| opening group | 237 | 70 | 29.53 | 142 | 29.91 | 25 | 10.54 | 89.45 |

The Radit Analysis Between Control Group and Treat Group u=3.5901 (u is the Figure of Statistic Checking, the Follow is Sameness)

4.2 Syndrome curative effect: The 438 cases of this group include excessive rise of liver-yang syndrome 246 cases, internal stagnation of the blood syndrome 192 cases. The general effective rate of Daxiong capsule to treat excessive rise of liver-yang syndrome is 90.91%, to internal stagnation of the blood syndrome is 86.75%. (Table 18)

TABLE 18

Syndrome curative effect analysis

| | Treat group | | | | control group | | | | opening group | | | |
|---|---|---|---|---|---|---|---|---|---|---|---|---|
| | apparent | efficacy | inefficacy | effective rate | apparent | efficacy | inefficacy | effective rate | apparent | efficacy | inefficacy | effective rate |
| excessive rise of liver-yang | 17 | 30 | 4 | 92.15 | 8 | 33 | 18 | 69.49 | 42 | 81 | 13 | 90.4 |
| internal stagnation of the blood | 15 | 27 | 8 | 84.00 | 3 | 28 | 10 | 75.60 | 27 | 61 | 12 | 88.0 |

The radit analysis between control group and treat group before and after therapy:

excessive rise of liver-yang: u=3.0202, p<0.01;
internal stagnation of the blood: u=2.0502, p<0.05.

4.3 The reduction of headache paroxysm times before and after therapy: According to the observation, Daxiong capsule can obviously reduce and relieve headache paroxysm times, Daxiong capsule can obviously reduce the headache paroxysm times. In contrast to the control group, there was very remarkable difference (p<0.001), the excessive rise of liver-yang syndrome group and internal stagnation of the blood syndrome group also have very remarkable difference (p<0.001) to control group. (Details shown in Tables 19-1, 19-2, 19-3).

TABLE 19-1

Headache paroxysm times before and after therapy (Every month)

| | | normal | | 1 time | | 2 time | | 3 time and more | |
|---|---|---|---|---|---|---|---|---|---|
| | Case number | Before therapy | After therapy | Before therapy | After therapy | Before therapy | After therapy | Before therapy | After therapy |
| Treat group | 101 | 0 | 56 | 2 | 36 | 35 | 4 | 64 | 5 |
| control group | 100 | 0 | 22 | 8 | 48 | 37 | 23 | 55 | 7 |
| opening group | 237 | 0 | 50 | 10 | 145 | 63 | 23 | 164 | 19 |
| total | 438 | 0 | 128 | 20 | 229 | 135 | 50 | 283 | 31 |

The radit analysis between control group and treat group after therapy: u=4.7887, p<0.001;
The radit analysis of treat group before and after therapy: u=11.2008, p<0.001.

TABLE 19-2

The excessive rise of liver-yang syndrome headache paroxysm times before and after therapy (Every month)

| | | normal | | 1 time | | 2 time | | 3 time and more | |
|---|---|---|---|---|---|---|---|---|---|
| | 例 | Before therapy | After therapy | Before therapy | After therapy | Before therapy | After therapy | Before therapy | After therapy |
| Treat group | 51 | 0 | 31 | 2 | 17 | 17 | 2 | 32 | 1 |
| control group | 59 | 0 | 16 | 6 | 29 | 15 | 12 | 38 | 2 |
| opening group | 136 | 0 | 37 | 8 | 76 | 33 | 14 | 95 | 9 |

The radit analysis between control group and treat group after therapy: u=3.4804, p<0.001
The radit analysis of treat group before and after therapy: u=8.2566, p<0.001

TABLE 19-3

The internal stagnation of the blood syndrome headache paroxysm times before and after therapy (Every month)

| | Number of case | normal | | 1 time | | 2 time | | 3 time and more | |
|---|---|---|---|---|---|---|---|---|---|
| | | Before therapy | After therapy | Before therapy | After therapy | Before therapy | After therapy | Before therapy | After therapy |
| Treat group | 50 | 0 | 25 | 0 | 19 | 18 | 2 | 32 | 1 |
| control group | 41 | 0 | 6 | 2 | 19 | 22 | 11 | 17 | 5 |
| opening group | 101 | 0 | 13 | 2 | 69 | 30 | 9 | 69 | 10 |

The radit analysis between control group and treat group after therapy; u=3.5333, p<0.001

The radit analysis of treat group before and after therapy: u=7.5933, p<0.001

4.4 The improvement of headache paroxysm degree before and after therapy:

According to the observation of 438 cases of vascular headache patients, with regard to the improvement of headache paroxysm degree before and after therapy, there was very remarkable difference (p<0.001) between control group and treat group. The excessive rise of liver-yang syndrome group and internal stagnation of the blood syndrome group also showed a very remarkable difference (p<0.001) to control group. (Details are shown in Tables 19-1, 19-2, 19-3)

TABLE 20-1 the improvement of headache paroxysm degree before and after therapy

| | Case number | normal | | Light | | medium | | serious | |
|---|---|---|---|---|---|---|---|---|---|
| | | Before therapy | After therapy | Before therapy | After therapy | Before therapy | After therapy | Before therapy | After therapy |
| Treat group | 101 | 0 | 55 | | 34 | 56 | 10 | 45 | 2 |
| control group | 100 | 0 | 17 | | 34 | 59 | 45 | 41 | 4 |
| opening group | 237 | 0 | 49 | 5 | 142 | 97 | 35 | 135 | 11 |
| total | 438 | 0 | 121 | 5 | 210 | 212 | 90 | 221 | 17 |

The radit analysis between control group and treat group after therapy: u=6.0677, p<0.001

The radit analysis of treat group before and after therapy: u=11.2594, p<0.001

TABLE 20-2

The improvement of the excessive rise of liver-yang syndrome headache paroxysm degree before and after therapy

| | Case number | normal | | Light | | medium | | serious | |
|---|---|---|---|---|---|---|---|---|---|
| | | Before therapy | After therapy | Before therapy | After therapy | Before therapy | After therapy | Before therapy | After therapy |
| Treat group | 51 | 0 | 32 | | 15 | 30 | 3 | 21 | 1 |
| control group | 59 | 0 | 10 | | 20 | 31 | 26 | 28 | 3 |
| opening group | 136 | 0 | 34 | 3 | 76 | 58 | 21 | 75 | 5 |

The radit analysis between control group and treat group after therapy: u=5.1654, p<0.001

The radit analysis of treat group before and after therapy: u=8.1727, p<0.001

TABLE 20-3 the improvement of the internal stagnation of the blood syndrome headache paroxysm degree before and after therapy

|  | Case number | normal | | Light | | medium | | serious | |
|---|---|---|---|---|---|---|---|---|---|
|  |  | Before therapy | After therapy | Before therapy | After therapy | Before therapy | After therapy | Before therapy | After therapy |
| Treat group | 50 | 0 | 23 |  | 19 | 26 | 7 | 24 | 1 |
| control group | 41 | 0 | 7 |  | 14 | 28 | 19 | 13 | 1 |
| opening group | 101 | 0 | 15 | 2 | 66 | 39 | 14 | 60 | 6 |

The radit analysis between control group and treat group after therapy: u=3.4051, p<0.001

The radit analysis of treat group before and after therapy: u=7.7665, p<0.001

5. Clinical Examination Standard Analysis 5.1 The Changes of Plasma 5-serotonin (5-HT) Before and After Therapy We observed 349 cases of all 438 cases for changes of plasma 5-serotonin (because one of the hospitals chose not have this examination). We divided the 349 cases into high-value group and low-value group according to the examination result before therapy, and observed the improvement after therapy. The statistics showed the improvement of treat group is very remarkable (p<0.001) before and with therapy in low-value group, there was very remarkable difference (p<0.05) between control group and treat group, but because we did not get enough data about syndrome divide group to explain the general effect rate, we did not divide into two syndrome groups as before, the same as follow data.

TABLE 21

The changes of 5-serotonin (5-HT) before and after therapy analysis

|  | Case number | Before therapy | After therapy |
|---|---|---|---|
| Treat group | 66 | 109.68 ± 125.57 | 105.19 ± 92.77 |
| control group | 65 | 124.94 ± 159.18 | 96.69 ± 107.93 |
| opening group | 218 | 100.74 ± 121.64 | 58.23 ± 37.40 |

The comparison between control group and treat group: t=0.48 (t is the figure of statistic checking, the follow is sameness) p<0.05.

TABLE 22

The changes of 5-serotonin (5-HT) analysis according to groups

|  | low-value group (<46) | | | high-value group (>46) | | |
|---|---|---|---|---|---|---|
|  | Case number | Before therapy | After therapy | Case number | Before therapy | After therapy |
| Treat group | 20 | 32.30 ± 9.00 | 56.73 ± 25.86 | 16 | 143.32 ± 137.57 | 126.26 ± 103.20 |
| control group | 17 | 32.16 ± 7.65 | 36.22 ± 16.89 | 48 | 157.79 ± 173.98 | 117.40 ± 118.70 |
| opening group | 43 | 29.09 ± 9.30 | 52.78 ± 27.67 | 175 | 118.35 ± 129.82 | 59.56 ± 39.38 | low-value group:

The comparison between control group and treat group after therapy: t=2.52, p<0.05

The comparison of treat group before and after therapy: t=3.71, p<0.001 high-value group:

The comparison between control group and treat group after therapy: t=0.39, p>0.05

The comparison of treat group before and after therapy: t=0.88, p<0.05

5.2 The Changes of Plasma Thromboxane ($TXB_2$) Before and After Therapy

We observed 428 cases of all 438 cases the changes of plasma thromboxane ($TXB_2$) before and after therapy. Statistics showed there is a very remarkable difference before and after therapy (p<0.001). We divided the 428 cases into high-value group and low-value group according to the examination result before therapy, and observed the improvement after therapy. Statistics showed that the improvement of treat group is very remarkable (p<0.001) before and after the therapy in high-value group. Tables 23 and 24 show the results.

TABLE 23

The changes of thromboxane ($TXB_2$) before and after therapy analysis

|  | Case number | Before therapy | After therapy |
|---|---|---|---|
| Treat group | 98 | 200.15 ± 110.29 | 149.53 ± 51.41 |
| control group | 94 | 189.96 ± 102.39 | 163.63 ± 91.73 |
| opening group | 236 | 176.66 ± 105.32 | 131.72 ± 55.21 |

The comparison between control group and treat group after therapy: t=1.32, p>0.05;

The comparison of treat group before and after therapy: t=4.78, p>0.001.

TABLE 24

The changes of thromboxane ($TXB_2$) analysis according to groups

|  | low-value group (<136) | | | high-value group (>136) | | |
|---|---|---|---|---|---|---|
|  | Case number | Before therapy | After therapy | number | Before therapy | After therapy |
| Treat group | 22 | 100.92 ± 25.00 | 115.86 ± 44.13 | 76 | 228.87 ± 108.78 | 159.28 ± 49.43 |
| control group | 17 | 102.47 ± 21.77 | 133.83 ± 21.23 | 77 | 209.28 ± 103.14 | 170.20 ± 97.48 |
| opening group | 72 | 69.50 ± 41.76 | 113.05 ± 49.25 | 164 | 223.71 ± 89.06 | 139.98 ± 55.83 | low-value group:

The comparison between control group and treat group after therapy: t=1.15, p<0.05;

The comparison between control group and treat group after therapy: t=1.15, p<0.05;

high-value group:

The comparison between control group and treat-group after therapy: t=0.88, p>0.05;

The comparison of treat group before and after therapy: t=5.56, p<0.001.

5.3 The Changes of Plasma Prostacyclin (PGFla) Before and After Therapy

We observed 428 cases of all 438 cases the changes of plasma prostacyclin (PGFla) before and after therapy. We divided the 428 cases into high-value group and low-value group according to the examination result before therapy. There is no difference (p>0.05) between the two groups. Observing the improvement after therapy, statistics showed the improvement of treat group is very remarkable (p<0.001) before and therapy in high-value and low-value group. Tables 25 and 26 show the results.

TABLE 25

The changes of PGFla before and after therapy analysis

|  | Case number | Before therapy | After therapy |
| --- | --- | --- | --- |
| Treat group | 98 | 28.91 ± 18.02 | 29.56 ± 13.56 |
| control group | 94 | 29.84 ± 15.02 | 29.57 ± 15.64 |
| opening group | 236 | 29.57 ± 16.55 | 24.54 ± 10.36 |

The comparison between control group and treat group after therapy: t=0.01, p>0.05;

The comparison of treat group before and after therapy: t=0.32, p>0.05

TABLE 26

The changes of PGFla analysis according to groups

| | low-value group (<23.9) | | | high-value group (>23.9) | | |
| --- | --- | --- | --- | --- | --- | --- |
|  | Case number | Before therapy | After therapy | Case number | Before therapy | After therapy |
| Treat group | 44 | 14.66 ± 4.49 | 26.46 ± 6.75 | 54 | 40.51 ± 16.50 | 32.09 ± 16.88 |
| control group | 22 | 16.68 ± 6.19 | 26.40 ± 18.66 | 72 | 33.86 ± 14.63 | 30.55 ± 14.60 |
| opening group | 98 | 14.08 ± 5.62 | 22.13 ± 10.15 | 138 | 40.58 ± 18.40 | 26.25 ± 10.20 | low-value group:

The comparison between control group and treat group after therapy: t=0.54, p<0.05

The comparison of treat group before and after therapy t=11.95, p<0.001;

high-value group:

The comparison between control group and treat group after therapy: t=0.88, p>0.05;

The comparison of treat group before and after therapy: t=2.75, p<0.01;

5.4 The Analysis of Blood Rheology Changes, Before and After Therapy

Because two of the hospitals did not have the blood rheology examination, we only observed 206 cases of all the 438 cases. Before and after therapy, we found that all cases we observed have different degree descent with packed cell volume, whole blood viscosity, whole blood deacidizing viscosity and plasma viscosity after therapy, but the statistics show no difference (p>0.05). Details are shown in Table 27.

TABLE 27

The changes of blood rheology before and after therapy analysis (X ± SD)

| | | Case number | packed cell volume | whole blood viscosity | whole blood deacidizing viscosity | plasma viscosity |
| --- | --- | --- | --- | --- | --- | --- |
| Treat group | Before therapy | 58 | 44.98 ± 3.82 | 6.88 ± 1.48 | 10.57 ± 11.14 | 3.57 ± 9.25 |
| | After therapy | 59 | 59.40 ± 3.21 | 6.25 ± 1.12 | 7.91 ± 0.80 | 1.67 ± 0.15 |
| control group | Before therapy | 57 | 43.53 ± 4.17 | 6.70 ± 1.38 | 8.86 ± 1.37 | 1.81 ± 0.14 |
| | After therapy | 59 | 41.73 ± 4.18 | 6.24 ± 1.16 | 11.14 ± 15.56 | 1.71 ± 0.17 |
| opening group | Before therapy | 142 | 44.58 ± 7.61 | 7.01 ± 5.83 | 11.51 ± 3.38 | 1.91 ± 1.36 |
| | After therapy | 141 | 41.05 ± 9.65 | 5.96 ± 5.83 | 9.58 ± 3.31 | 1.90 ± 2.55 |

The comparison between control group and treat group after therapy:

packed cell volume: t=1.09, P>0.05 whole blood viscosity: t=0.05, P>0.05 whole blood deacidizing viscosity: t=1.60, P>0.05 plasma viscosity: t=1.40, P>0.05

5.5 The Analysis of the Platelets Aggregation's Changes, Before and After Therapy Because three of the hospitals did not have the platelets aggregation examination, we only observed 142 cases of all the 438 cases. Before and after therapy, we found that all cases in three groups have different degree descent with platelets aggregation, but statistics show no difference. Details are shown in Table 28.

TABLE 28

The changes of platelets aggregation before and after therapy analysis

|  | Case number | Before therapy | After therapy |
|---|---|---|---|
| Treat group | 30 | 59.20 ± 13.11 | 49.92 ± 7.60 |
| control group | 30 | 57.18 ± 17.35 | 51.79 ± 12.35 |
| opening group | 82 | 67.67 ± 20.65 | 49.21 ± 17.05 |

The comparison between control group and treat group after therapy: t=0.7 1, P>0.05

5.6 The Analysis of the Doppler Colorful Ultrasound's (TCD) Changes, Before and After Therapy In all 438 cases, some hospitals do Doppler colorful ultrasound (TCD) on patients. We observed in 259 cases the changes before and after therapy with TCD, include treat group 65 cases, control group 65 cases, opening group 129 cases, and found that the improvement of treat group is very remarkable (p<0.001) before and after therapy. There is also a remarkable difference between treat group and control group (P<0.01). Details are shown in Table 29.

TABLE 29

The improvement of TCD before and after therapy

|  | Case number | Before therapy | | | | After therapy | | | | Effective rate (%) |
|---|---|---|---|---|---|---|---|---|---|---|
|  |  | serious | medium | light | normal | serious | medium | light | normal |  |
| Treat group | 65 | 2 | 27 | 31 | 5 | 2 | 14 | 16 | 33 | 87.7 |
| control group | 65 | 2 | 29 | 27 | 7 | 2 | 23 | 29 | 11 | 85.1 |
| opening group | 129 | 5 | 50 | 36 | 35 | 5 | 31 | 32 | 16 | 86.9 |

The comparison between control group and treat group after therapy: u=3.1518, P<0.01

The comparison of treat group before and after therapy: u=4.1195, P<0.001

5.7 The Analysis of the Rheoencephalogram's (REG) Changes, Before and After Therapy In all 438 cases, we observed 184 cases the changes before and after therapy with REG, including treat group 30 cases, opening group 154 cases. We found that the improvement of treat group is very remarkable (p<0.001) before and after therapy. Details are shown in Table 30.

TABLE 30

The improvement of REG before and after therapy

| Group name | case number | Before therapy | | | After therapy | | | effective rate (%) |
|---|---|---|---|---|---|---|---|---|
|  |  | hyperkinesia | low-flat | normal | hyperkinesia | low-flat | normal |  |
| Treat group | 30 | 2 | 24 | 4 |  | 14 | 16 | 87.0% |
| opening group | 154 | 12 | 128 | 15 | 3 | 77 | 74 | 88.4% |

The comparison of treat group before and after therapy: u=2.8926, P<0.01

6. Conclusion

The clinical experiment proved that Daxiong capsule have obvious improvement with Chinese medicine syndrome, clinical symptom, laboratory standard, etc. The average effective rate of Daxiong capsule is 89.05%, while Yuntongding is 72%. Daxiong capsule is obviously higher than Yuntongding, the statistics showed there is remarkable different between the two groups (P<0.001), proved that Daxiong capsules have the efficiency of promoting blood flow and the circulation of Qi, calming the liver and harmonizing the link, dispelling pathogenic wind and alleviating pain. It has good effectiveness to the patient with excessive rise of liver-yang and internal stagnation of the blood syndrome. We proved that Daxiong capsule is a good medicine to vascular headache with excessive rise of liver-yang (the effective rate is 90.91%) and internal stagnation of the blood syndrome (the effective rate is 86.75%).

Industrial Application

The medicine combination of this invention about headache treatment can avoid blood coagulation to the blood system, can lower the blood-pressure and myocardium oxygen-consumption to cardiovascular system, can calm and alleviate pain to nervous system. The clinical trial proved that the effective rate of this medicine to treat vascular headache with excessive rise of liver-yang is 90.91%, to internal stagnation of the blood syndrome is 86.75%. The invention's medicine prescription is convenient. It can be made into a variety of dosage forms such as the capsule, water-solvable-powder, tablet, oral liquid, pill, drop pills, etc by the normal preparation. It has good industrial application.

What is claimed is:

1. A method for preparing a pharmaceutical composition made of herbs based on the following weight proportion:

rhizome of chuanxiong 10 g–25 g, and
rhizome of tall gastrodia 1.5 g–8 g;

the method comprising:

(1) dehydrating, smashing, and mixing together rhizome of chuanxiong and rhizome of tall gastrodia to obtain a mixed powder of rhizome of chuanxiong and rhizome of tall gastrodia;

(2) reflux extracting the mixed powder of rhizome of chuanxiong and rhizome of tall gastrodia with 90% alcohol solution at least once to extract at least one reflux extracted solution;

(3) if the mixed powder of rhizome of chuanxiong and rhizome of tall gastrodia is reflux extracted more than once, then the reflux extracted solutions are merged into one reflux extracted solution;

(4) filtering the reflux extracted solution to obtain a reflux filtrate;

(5) condensing the reflux filtrate to a clear cream at a relative density of 1.27 and at a temperature ranging from 55° C. to 60° C.;

(6) cooking the gruffs remaining from the alcohol extraction of step (2) of rhizome of chuanxiong and rhizome of tall gastrodia with water at least once to obtain at least one cooked extracted solution;

(7) if the gruffs of rhizome of chuanxiong and rhizome of tall gastrodia are cooked more than once, then the cooked extracted solutions are merged into one cooked extracted solution;

(8) filtering the cooked extracted solution to obtain a cooked filtrate;

(9) condensing the cooked filtrate to clear cream at a relative density of 1.27 and at a temperature ranging from 55° C. to 60° C.;

(10) combining the clear creams from steps (5) and (9) together;

(11) adding excipient to the combined clear cream; and

(12) vacuum dehydrating; smashing; and filtering the cream.

2. The method for preparing a pharmaceutical composition of claim 1, wherein the amount of the rhizome of chuanxiong is 8 g–15 g and wherein the amount of rhizome of tall gastrodia is 2 g–6 g.

3. The method for preparing a pharmaceutical composition of claim 1, wherein the amount of the rhizome of chuanxiong is 10 g and wherein the rhizome of tall gastrodia is 2.5 g.

4. The method of claim 1, wherein the 90% alcohol solution is used twice to extract mixed raw herbs powder and wherein the gruffs are cooked twice.

5. A method of claim 4, wherein the 90% alcohol solution is used twice to extract mixed raw herbs powder, each time for 2 hours, and wherein the gruffs are cooked twice, each time for 1 hour.

6. The method of claim 1, wherein the preparation is in the form of a capsule, a water-solvable-powder, a tablet, an oral liquid, a pill, or a drop pill.

7. A method for treating vascular headache using a pharmaceutical composition prepared in accordance with any one of claims 1–3, comprising administering the pharmaceutical composition to a patient in need thereof.

8. A method for treating neural headache using a pharmaceutical composition prepared in accordance with any one of claims 1–3, comprising administering the pharmaceutical composition to a patient in need thereof.

9. A method for treating anoxia using a pharmaceutical composition prepared in accordance with any one of claims 1–3, comprising administering the pharmaceutical composition to a patient in need thereof.

10. A method for treating hypertension using a pharmaceutical composition prepared in accordance with any one of claims 1—3, comprising administering the pharmaceutical composition to a patient in need thereof.

11. A method for inhibiting platelet aggregation using a pharmaceutical composition prepared in accordance with any one of claims 1–3, comprising administering the pharmaceutical composition to a patient in need thereof.

12. A method for inhibiting the development of thrombosis using a pharmaceutical composition prepared in accordance with any one of claims 1–3, comprising administering the pharmaceutical composition to a patient in need thereof.

13. A method for inhibiting blood coagulation using a pharmaceutical composition prepared in accordance with any one of claims 1–3, comprising administering the pharmaceutical composition to a patient in need thereof.

* * * * *